United States Patent
Jordao Coelho et al.

(10) Patent No.: US 11,932,719 B2
(45) Date of Patent: Mar. 19, 2024

(54) PHOTOPOLYMERIZED BIODEGRADABLE COPOLYMER FORMULATIONS FOR BIOMEDICAL APPLICATIONS

(71) Applicants: UNIVERSIDADE DE COIMBRA, Coimbra (PT); UNIVERSIDADE DO PORTO, Oporto (PT)

(72) Inventors: Jorge Fernando Jordao Coelho, Coimbra (PT); Ana Clotilde Amaral Loureiro Da Fonseca, Coimbra (PT); Armenio Coimbra Serra, Coimbra (PT); Ana Catarina Da Silva Pinho, Coimbra (PT); Jose Domingos Santos, Oporto (PT); Ana Colette Pereira De Castro Osorio Mauricio, Oporto (PT); Ana Rita Caseiro Santos, Oporto (PT); Silvia Marlene Almeida Santos Pedrosa, Oporto (PT); Mariana Esteves Vieira Branquinho, Oporto (PT); Rui Damasio Alvites, Oporto (PT); Irina Ferraz Amorim Cruz, Oporto (PT)

(73) Assignees: UNIVERSIDADE DE COMIBRA, Coimbra (PT); UNIVERSIDADE DO PORTO, Oporto (PT)

(*) Notice: Subject to any disclaimer, the term of this patent is extended or adjusted under 35 U.S.C. 154(b) by 698 days.

(21) Appl. No.: 16/972,699

(22) PCT Filed: Jun. 6, 2019

(86) PCT No.: PCT/IB2019/054735
§ 371 (c)(1),
(2) Date: Dec. 7, 2020

(87) PCT Pub. No.: WO2019/239266
PCT Pub. Date: Dec. 19, 2019

(65) Prior Publication Data
US 2021/0253771 A1 Aug. 19, 2021

(30) Foreign Application Priority Data

Jun. 11, 2018 (PT) .......................... 110781

(51) Int. Cl.
*C08F 299/04* (2006.01)
*A61L 27/34* (2006.01)
*C08K 5/05* (2006.01)
*A61B 17/11* (2006.01)

(52) U.S. Cl.
CPC ........ *C08F 299/0492* (2013.01); *A61L 27/34* (2013.01); *C08K 5/05* (2013.01); *A61B 17/1128* (2013.01); *C08G 2230/00* (2013.01)

(58) Field of Classification Search
CPC ............. C08C 37/0021; C08F 299/026; C08G 18/8116
See application file for complete search history.

(56) References Cited

PUBLICATIONS

Van Dijk-Wolthuis et al., Macromolecules, 1995, 28, 6317-6322.*
Friess et al., Adv Healthcare Mater, 2014, 3, 1986-1990.*
Wang et al., Macromol Symp, 2014, 346, 82-90.*

* cited by examiner

*Primary Examiner* — Kyle A Purdy
(74) *Attorney, Agent, or Firm* — Rivka Friedman (57) ABSTRACT

A biodegradable based polymers for the production of biodegradable medical applications is provided. The biobased material has a copolymer constituted by dextran modified with glycidyl methacrylate and poly (#-caprolactone) modified with 2-isocyanatoethylmethacrylate, which are combined in different formulations and used to produce membranes, 3-D scaffolds and hollow tubes that can be used as biomedical devices for diverse applications, such as drug delivery systems, tissue engineering scaffolds, repair and regeneration of peripheral nerves, among others.

18 Claims, 8 Drawing Sheets

PHOTOPOLYMERIZED BIODEGRADABLE COPOLYMER FORMULATIONS FOR BIOMEDICAL APPLICATIONS

CROSS-REFERENCE TO RELATED APPLICATIONS

This application is a 371 of PCT/IB2019/054735, filed Jun. 6, 2019, which claims the benefit of Portuguese Patent Application No. 110781, filed Jun. 11, 2018, each of which are incorporated herein by reference.

TECHNICAL FIELD

This application relates to copolymers, their production and medical applications thereof.

BACKGROUND ART

Tubulization techniques have been proposed as good alternatives to enhance nerve regeneration after injury. The scope of this technique relies on the use of a hollow tube, which is sutured to both nerve ends to guide the newly formed axons from distal to proximal stump. Biocompatible polymeric materials, due to their physicochemical and biological characteristics, have been used for the preparation of this particular type of medical device. In this sense, dextran, a bacterial derived polysaccharide, which is biocompatible, arises as a good candidate for the preparation of devices suitable for tissue regeneration related applications (Radiat Phys Chem 142 (2018) 115-120 and Inżynieria i Aparatura Chemiczna (2014) 251-252).

Moreover, this natural polymer has been widely used in the biomedical field, as core material of surgical adhesives (Acta Biomaterialia 53 (2017) 343-354) and hydrogels for tissue regeneration purpose (Radiat Phys Chem 142 (2018) 115-120). Furthermore, dextran degrades under physiological environment and its degradation products are considered to be non-toxic. The degradation occurs through the action of the dextranase enzyme in organs such as liver, spleen, kidneys and colon (Biol Pharm Bull 20 (1997) 181-187). However, albeit its interesting advantages, dextran presents poor mechanical properties (J. Mater. Chem. B 2 (2014) 8346-8360 and Adv Healthc Mater. 5 (2016) 2732-2744) and hence its modification is often needed (Carbohydr Polym 82 (2010) 412-418 and Carbohydr Polym 114 (2014) 467-475).

Poly (ε-caprolactone) (PCL) is a bioresorbable, hydrophobic and semi-crystalline polyester (Biomaterials 26 (2005) 4817-4827). Its tailorable degradation and mechanical properties, along with its good compatibility, have made this polymer very attractive to the biomedical field since the 1970s. During this time, it was used in various drug delivery systems, but as its degradation rate was slow, other resorbable polymers as PGA and poly(D,L-lactide) (PDLA) were preferred. However, since the 2000s, with the rising of tissue engineering techniques, PCLs has been extensively tested both in vitro and in vivo revealing good results in terms of biocompatibility. Specifically, for peripheral nerve regeneration, this polymer, like other bioabsorbable polymers, has been tested in nerve guides alone mixed with other polymers and seeded with both cells and nerve growth factors. Nerve guides prepared with PCL-PVA (J Mater Sci Mater Med 24 (2013) 1639-1647), PCL with encapsulated neurotrophic factor derived from glial cell (GDNF) (ACS Biomater Sci Eng. 1 (2015) 504-512), PCL surfaces functionalized with peptides as RGD (N. Biotechnol 31 (2014) 203-213), are some examples. Unfortunately, problems associated with slow degradation rate are still mentioned. Due to the possibility of tailoring the properties of the present technology, the described embodiments can also be applied to other biomedical applications where the degradation ratio plays an important role. Such applications comprise biomedical tubes for stenting purposes; biomedical sheets for intra-corporeal application; biomedical sheaths for needles and tubes, which are introduced into the body; particles and plugs for embolization purposes; vascular prosthesis; tissue engineering scaffolds; artificial skin and (micro)spheres for targeting drug delivery. Specifically, for the last example, there is an increased effort to create non-invasive and painless administration routes for the administration of drugs. In this sense, drug delivery systems with different geometries and sizes have been proposed to overcome the major disadvantages of the oral route (Prog Polym Sci 39 (2014) 2030-2075). The Research has been conducted based on the exploration of new administration routes and developing new polymeric materials that could match the requirements of each drug for the specific target.

SUMMARY

The present application relates to photopolymerized biodegradable copolymer formulations comprising dextran modified with glycidylmethacrylate and poly ε-caprolactone modified with 2-isocyanatoethyl methacrylate.

In one embodiment the percentage of the modified dextran ranges between 25% and 50% (w/w).

In another embodiment the percentage of the modified poly ε-caprolactone ranges between 50% and 75% (w/w).

In yet another embodiment the formulations further comprise water soluble sugar-type or salt-type known porogenic agents.

In one embodiment the porogenic agent is selected from a list comprising sucrose, sodium chloride and sodium carbonate.

In another embodiment the porogenic agent is D-mannitol.

In one embodiment the content of D-mannitol ranges between 20 and 80% (w/w) of the copolymer formulation.

In one embodiment the copolymer formulation is shaped into films, sheets, tubes, rods, plugs, microspheres or meshes.

In one embodiment the copolymer formulations are solid.

The present application also relates to a method of photopolymerization to prepare solid materials from copolymer formulations, comprising the following steps:
  dextran modified with glycidyl methacrylate is dissolved in DMSO at room temperature;
  poly ε-caprolactone modified with 2-isocyanatoethyl methacrylate is added to the previous solution;
  complete dissolution of the previous co-macromonomers and addition of a photoinitiator;
  the formulation is left to photocrosslink under UV light with a wavelength of 280 nm;
  the final copolymer is washed with water for a period up to 7 days and then dried under vacuum.

In one embodiment dextran is used in a range up to 200000 g/mol.

In another embodiment dextran 70000 g/mol is used.

In one embodiment poly ε-caprolactone is used in a range up to 600 g/mol.

In one embodiment the final copolymer formulations are dried at 40° C.

In one embodiment the photoinitiator is used in a concentration between 0.02 and 2% (w/v).

In another embodiment after complete dissolution of the co-macromonomers, a water soluble sugar-type or salt-type known porogenic agent is added to the solution and left to solubilize.

In yet another embodiment the photopolymerized copolymer comprising the porogenic agent are immersed in distilled water and left in an oven at 37° C. for 3 days, before washing the final copolymer with water and drying under vacuum.

Additionally, the present application also relates to photopolymerized biodegradable copolymer formulations for use in biomedical applications.

In one embodiment the photopolymerized biodegradable copolymer formulations are for use in regenerative medicine.

In another embodiment the photopolymerized biodegradable copolymer formulations are for use as nerve guides.

In yet another embodiment the photopolymerized biodegradable copolymer formulations are for use as biomedical drains, biomedical tubes for stenting purposes, biomedical sheets for intra-corporeal application such as an anti-adhesive sheet, biomedical sheets for topical use such as temporary wound care coverage or to prevent scarring, wound care foams, protective sheaths for needles and tubes which are introduced into the body, (micro)spheres for drug delivery, (micro)spheres, particles and plugs for embolization purposes, (micro)spheres for cosmetic surgical purposes, such as dermal augmentation, treatment of wrinkles and skin contour deficiencies, vascular prostheses, tissue engineering scaffolds, artificial skin or scaffolding plug for meniscus repair.

General Description

To this day there is still a lack of suitable polymers with the required properties to be used in regenerative medicine. Therefore, the aim of the present technology is to provide a dextran based material, which covers the requirements for its use in regenerative medicine, including the peripheral nerve regeneration, mostly in neurotmesis injuries where an end-to-end suture is not possible. For this purpose, dextran was modified by incorporating double bonds by its reaction with glycidyl methacrylate (GMA). In an embodiment this reaction requires low reaction times in order to modulate the amount of dextran modification (Macromolecules 28 (1995) 6317-6322). The product of this reaction is Dextran-GMA.

In order to fine tune the properties of the desired material, a Poly (ε-caprolactone) (PCL) dimethacrylate co-macromonomer is added to a formulation comprising Dextran-GMA.

In an embodiment the PCL dimethacrylate co-macromonomer is obtained from the reaction of PCL with hydroxyl terminal groups with IEMA, resulting in PCL-IEMA (Int. J. Pharm 352 (2008) 172-181)).

Addressing the influence of co-macromonomers content in the final copolymers properties was also the object of the present technology.

The formulations with PCL-IEMA and dextran-GMA are crosslinked by UV light irradiation originating the final material, a copolymer, with unique properties to be used in medical applications.

The dextran modification with glycidyl methacrylate was proved by the $^1$H NMR spectrum of Dextran-GMA in $D_2O$, apart from the typical peaks of dextran polymer, additional ressonances ascribed to the protons of the double bonds, and protons of the —$CH_3$ group belonging to the methacrylate group were observed. The percentage of modification of dextran was calculated from the relation between the integrals values of the signals corresponding to dextran and to the double bond of GMA. The values obtained are in the range of 31-34% (Macromolecules 28 (1995) 6317-6322).

In the case of the modification reaction of PCL, all added IEMA was consumed in the reaction. This was confirmed by FT-IR where the strong band characteristic of isocyanate group was not visible.

It was found that the combination of the two materials described above, Dextran-GMA and PCL-IEMA and their copolymerization by a photocrosslink reaction would give a new product with the required characteristics for the final material to be used in regenerative medicine.

Additionally, to increase the porosity of the final material, the copolymers, it is possible to add D-mannitol without compromising the photopolymerization reaction and the copolymer integrity.

In order to access the mechanical and chemical characteristics of the copolymers produced, swelling capacity and degradation tests were performed. In vitro and in vivo tests were also performed to access the performance of the copolymers in medical applications, including peripheral nerve reconstruction and regeneration.

BRIEF DESCRIPTION OF DRAWINGS

For easier understanding of this application, figures are attached in the annex that represent the preferred forms of implementation which nevertheless are not intended to limit the technique disclosed herein.

The accompanying drawings illustrate various embodiments of the present technology and are a part of the specification. The illustrated embodiments are merely examples of the present invention and do not limit the scope of the technology.

FIG. 1 shows the FTIR spectra of Dextran, Dextran-GMA, PCL-diol and PCL-IEMA. FTIR spectra were obtained using a Jasco FT/IR-4200 spectrometer with ATR mode, at room temperature. Data were collected in the range 4000-500 cm−1 with 4 cm−1 spectral resolution and 64 accumulations.

The $^1$H NMR spectra were obtained at 25° C. on a Bruker Avance III 400 MH spectrometer using a triple detection TIX 5 mm probe. The $^1$H NMR spectra were obtained at 25° C. on a Bruker Avance III 400 MH spectrometer using a triple detection TIX 5 mm probe. For dextran and dextran-GMA, the solvent used was $D_2O$ and specific conditions were used, as described elsewhere (Macromolecules 28 (1995) 6317-6322). Briefly, a pulse angle of 87.7° was used with a relaxation delay of 30 s. The water signal at 4.8 ppm was eliminated by solvent suppression with decoupling. The decoupling power was adjusted to a level at which the intensity of the anomeric proton signal was not affected. For PCL-diol and PCL-IEMA, the solvent used was DMSO-d6. TMS was used as the internal standard.

The thermal stability of the materials was evaluated by thermogravimetric analysis (TGA) using a TA Instruments Q500 equipment. The range of temperatures between 25° C. and 600° C. was used. The heating rate of 10° C.·min$^{-1}$ and the analysis was performed under nitrogen atmosphere.

The thermal behavior of the materials before degradation was evaluated by Differential Scanning Calorimetry (DSC). The equipment used is a TA Instruments Q100, equipped with a RSC90 cooling unit.

Dextran and Dextran-GMA were first heated from 25° C. to 250° C., followed by a cooling cycle from 250° C. to −80° C. in order to eliminate their thermal history. The samples were then submitted to a second heating cycle from −80° C. to 250° C. In the case of PCL-diol and PCL-IEMA, the first heating cycle was performed from 25° C. to 150° C., followed by a cooling cycle until −80° C. The second heating cycle was performed from −80° C. to 150° C.

The heating rate was 10° C.·min$^{-1}$ and the analysis was done under N2 atmosphere (50 mL·min$^{-1}$). The mass of the samples was between 7 mg and 9 mg were used.

Also, curves obtained for Dextran-GMA and PCL-IEMA are included for comparison.

The thermal stability of the materials was evaluated by thermogravimetric analysis (TGA) using a TA Instruments Q500 equipment. The range of temperatures between 25° C. and 600° C. was used. The heating rate of 10° C.·min$^{-1}$ and the analysis was performed under nitrogen atmosphere.

The swelling capacity of circular membranes with 1 cm diameter was measured in PBS (pH=7.4, 0.01M). Dried samples with a known dried weight were immersed in 5 mL of PBS, at 37° C., until a swelling equilibrium was achieved. At predetermined times, the samples were taken out from the PBS, and the surface water gently blotted by filter paper.

The percentage of swelling capacity was calculated using the following equation: Swelling Capacity (%)=(W_s−W_d)/W_d×100 Where W_s is the weight of the swollen samples and W_d is the weight of the dried samples before the immersion in PBS. The measurements were conducted in triplicate.

FIG. 8 shows the in vitro hydrolytic degradation of copolymers of Dextran-GMA and PCL-IEMA. The following notation is used to indicate the co-macromonomer content percentage ratio in the final composition of the copolymers ([Dextran-GMA/PCL-IEMA]). Tests were performed in PBS (pH=7.4, 0.01M). Dried circular membranes with 1 cm diameter and with known weight were immersed in PBS, at 37° C., during 30 days. At predetermined times, the membranes were removed from PBS, rinsed with distilled water and dried until the stabilization of their weight.

The estimation of the degree of degradation was made through the calculation of the weight loss after incubation, according to the following equation: Weight Loss (%)= (W_0−W_t)/W_0×100

Where W_0 is the initial weight of the dry sample before being immersed and W_t is the weight of the dry sample after being immersed in PBS and dried. The measurements were conducted in triplicate.

Copolymers were fixed to each well in a 24-well cell culture plate, and relevant controls were prepared with the fixation agent alone (SG) and copolymers without cells. Then, materials were seeded at 4×10$^4$ cells/well density. Cells were left adhering in 0.5 mL of complete culture medium overnight. At every time point [24 hours (1 day), 72 hours (3 days), 120 hours (5 days) and 168 hours (7 days)] culture medium was removed from each well and fresh complete medium was added to each well, with 10% (v/v) of 10× Presto Blue® cell viability reagent. Cells were incubated for 1 hour at 37° C., 5% $CO_2$, changes in cell viability were detected by absorption spectroscopy in a Thermo Scientific Multiskan FC. Supernatant was collected and transferred to a 96-well plate and absorbance was read at 570 nm and 595 nm. After, cells were washed with PBS to remove any Presto Blue® residues and fresh culture medium is reset to each well. Presto Blue® excitation wavelength is 570 nm, and emission is at 595 nm. For each well, the absorbance at 595 nm (normalization wavelength) was subtracted to the absorbance at 570 nm (experimental result). Corrected absorbance is obtained by the subtraction of average of the control wells to each experimental well.

The percentage of swelling capacity was calculated using the same equation aforementioned.

The in vitro hydrolytic degradation was calculated using the same methodology mentioned in the description of FIG. 2.

FIG. 14 shows the withdrawal reflex obtained by the use of painful stimuli. The following notation is used to indicate the co-macromonomer content percentage ratio in the final composition of the copolymers, and content of D-Mannitol: [Dextran-GMA/PCL-IEMA](D-Mannitol).

DESCRIPTION OF EMBODIMENTS

Now, preferred embodiments of the present application will be described in detail with reference to the annexed drawings. However, they are not intended to limit the scope of this application.

The aim of the present technology is to provide a dextran based material, which covers the requirements such as biocompatibility, biodegradability, adequate permeability, appropriate biomechanical properties, surface properties and customized dimension, for its use in regenerative medicine.

To obtain a final material, initially, dextran was modified with incorporation of double bonds by its reaction with glycidyl methacrylate (GMA). First, 2.5 g ($1.54 \times 10^{-2}$ mol) of dextran were dissolved in 22.5 mL of dimethyl sulfoxide (DMSO) in a round bottom flask immersed in a water bath at 30° C. After the complete solubilization of dextran, 0.5 g ($4.09 \times 10^{-3}$ mol) of dimethylaminopyridine (DMAP) was dissolved in the solution and 2.05 mL ($1.54 \times 10^{-2}$ mol) of GMA was added. The reaction proceeded for 8 h under nitrogen atmosphere. After this time, to neutralize the solution, 0.33 mL of HCl 37% (w/w) was added. The product of the reaction was then dialyzed against water. The product was freeze dried, leading to a sponge-like product. This reaction yields a formulation of Dextran-GMA.

In the present technology, the use of dextran is preferred. In a preferred embodiment, dextran 70000 g/mol was used. Nevertheless, this parameter can be altered and other molecular weights can be used in a range up to 200000 g/mol. Furthermore, despite the fact that for the modification of the natural polymer, GMA was chosen in a preferred embodiment.

Following the previous reaction to obtain Dextran-GMA, a PCL dimethacrylate co-macromonomer was synthesized.

In a preferred embodiment, the PCL dimethacrylate was obtained from the reaction of PCL containing hydroxyl terminal groups with IEMA (PCL-IEMA). In a round bottom flask placed in a water bath at 40° C., 2.2 g (4 mmol) of PCL-diol were dissolved in 30 mL of tetrahydrofuran (THF), under nitrogen atmosphere. After PCL-diol solubilization, 1.27 g (8.2 mmol) of IEMA and 150 mg dibutyltin dilaurate (3 drops approx.) were added to the reaction mixture. The reaction was allowed to proceed for 24h. The product was recovered by precipitation in n-hexane and dried under vacuum, until constant weight, at room temperature.

In the present technology, the use of PCL containing hydroxyl terminal groups is preferred. In the present application, Poly ε-caprolactone is used in a range up to 600 g/mol.

Similarly, in a preferred embodiment IEMA is used to modify PCL.

After the preparation of Dextran-GMA and PCL-IEMA, formulations comprising different amount of both materials were prepared, in a range between 25:50 and 50:75 [Dextran-GMA:PCL-IEMA]. The copolymers were dissolved in 2 mL of DMSO till complete solubilization.

The final material is obtained by irradiating the formulations comprising PCL dimethacrylate (PCL-IEMA) and dextran-GMA with UV light (wavelength=280 nm), for 2 hours at room temperature, promoting a photocrosslink reaction between the two copolymers.

In the context of the present application room temperature is defined as the temperature between 15° C. and 25° C.

In the present technology, the irradiation with UV light is preferred, although, the final materials can also be obtained by additive manufacturing techniques as 3D printing using UV radiation, which allows to increase the complexity of the final shape and has been reported for the preparation of biomedical devices (Biofabrication 10 (2018) 1-20 and J. Neural Eng. 15 (2018) 1-12).

The photocrosslinking reaction is carried out with the combination of UV light and a photoinitiator in a concentration between 0.02-2% w/v. In one embodiment the photoinitiator concentration is 0.1% w/v.

In an embodiment the photoinitiator is Irgacure® 2959.

The resulting copolymers of this reaction, made with different relative amounts of Dextran-GMA and PCL-IEMA are transparent materials and their thermal-mechanical properties were found to be dependent on the co-macromonomer contents.

The shape of the materials can vary, depending on the mold. In a preferred embodiment membranes shape and hollow tube shape were prepared. However, with the present methodology, it is also possible to prepare these materials in a sphere shape, which is commonly used for drug delivery systems applications.

Copolymers with higher contents of PCL-IEMA show higher thermal stability (around 8% higher) and lower glass transition (between 64-93% lower), which translates into more flexible materials.

For medical applications, the porosity of these materials is an important parameter to have in consideration (Tissue Eng Part C Methods 19 (2013) 233-243).

It is reported that permeable tubes allow the exchange of nutrients and oxygen, allow the drainage of the tube and also, allow the vascularization inside the tube. All these factors have shown to have an important role on the enhancement of nerve regeneration (Tissue Eng Part C Methods 19 (2013) 233-243).

In one embodiment, porosity can be provided to the prepared materials by adding water soluble sugar-type or salt-type known porogenic agents as sucrose, sodium chloride and sodium carbonate.

From several tests with described porogenic agents (PLoS One 7 (2012) e48824), D-mannitol is able to give porosity to the materials without compromising the photopolymerization reaction and the copolymer integrity.

The presence of D-mannitol, in contents between 20-80% (w/w) of the copolymer formulation, does not disturb the photocrosslink reaction.

In one embodiment, the amount of D-mannitol added to formulation of Dextran-GMA:PCL-IEMA is 0% (w/w). In another embodiment, the amount of D-Mannitol added was 80% (w/w). In formulations with D-mannitol, it is added after complete solubilization of the dextran-GMA and PCL-IEMA in DMSO. When complete solubilization of D-mannitol is achieved, Irgacure®2959 is also added and solubilized. Then, the formulations are left to photocrosslink under UV light. After polymerization, the materials are immersed in distilled water and left in an oven at 37° C. for 3 days, to remove D-mannitol. Then, the final materials are washed with Milli-Q water for 7 days and dried under vacuum, at 40° C.

In summary, the method of photopolymerization to prepare the solid copolymer of Dextran-GMA and PCL-IEMA follows the following steps:
  dextran-GMA is dissolved in DMSO at room temperature;
  PCL-IEMA is added to the previous solution;
  complete dissolution of the previous co-macromonomers and addition of a photoinitiator;
  the formulation is left to photocrosslink under UV light with a wavelength of 280 nm;
  The final copolymer is washed with water for 7 days and then dried under vacuum.

The amount of Dextran-GMA used is between 25 and 50% (w/w). The amount of PCL-IEMA used is between 50 and 75% (w/w).

In a preferred embodiment the final materials are washed with Milli-Q water.

In a preferred embodiment the final materials are dried under vacuum at 40° C.

In one embodiment, Dextran-GMA is dissolved in 2 mL DMSO.

In one embodiment the formulation is left to photocrosslink for 1 hour.

In one embodiment, after complete dissolution of Dextran-GMA and PCL-IEMA, a water soluble sugar-type or salt-type known porogenic agent is added to the solution and left to solubilize. After the photocrosslinking step, the obtained copolymer is then immersed in distilled water and left in an oven at 37° C. for 3 days, to remove the porogenic agent, before washing the final copolymer with water and drying under vacuum.

Figure 1:
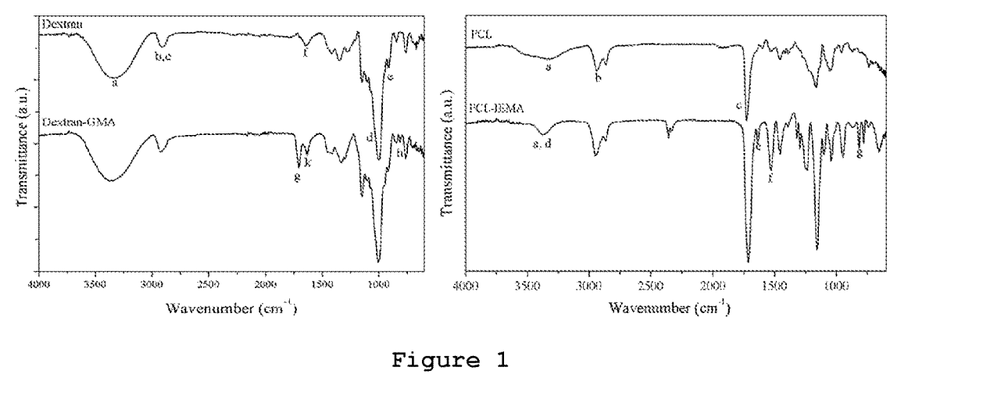

FTIR spectra of Dextran, Dextran-GMA, PCL-diol and PCL-IEMA: In the dextran spectrum it is possible to identify the typical bands found in this polysaccharide, namely the stretching vibration of —OH groups (a) which can be observed at 3300 cm$^{-1}$. At 2910 cm$^{-1}$ it is possible to observe the bands corresponding to the stretching vibration of both CH and CH2 groups (b and c, respectively). Between 1000-1100 cm$^{-1}$, there are the bands corresponding to the stretching vibration of ether linkages (d) and at 914 cm$^{-1}$ it is the band ascribed to the vibration of the α-glycosidic bond (e). 44 At 1636 cm$^{-1}$, it is possible to observe the band that corresponds to the bending of bound water (f).

Regarding the spectrum of Dextran-GMA, it is possible to observe some differences in relation to the spectrum of pristine dextran. A new band at ca. 1710 cm$^{-1}$ (g) corresponds to the stretching vibration of the carbonyl group of the ester linkage (present in GMA). The bending vibration of the methacrylate group can be seen in both spectra at 813 cm$^{-1}$ (h). The stretching vibration of the double bond can be seen at 1650 cm$^{-1}$.

In the PCL-diol spectrum, it is possible to identify the following bands: (a) 3340 cm$^{-1}$, corresponding to the vibration of —OH groups, (b) 2940 cm$^{-1}$ and 2865 cm$^{-1}$, corresponding to asymmetric and symmetric stretching of $CH_2$, respectively. The peak at (c) 1730 cm$^{-1}$ is ascribed to the stretching vibration of the —C═O group of the ester linkage.

In the spectrum of PCL-IEMA, it is possible to identify the characteristic bands of the urethane linkage, confirming the successful modification of the PCL-diol structure. The first of these bands is at (d) 1720 cm$^{-1}$, corresponding to the stretching vibration of the carbonyl group of the ester from PCL-diol, which is overlapped with the carbonyl group belonging to the urethane linkage. Then, at (e) 1630 cm$^{-1}$ is ascribed to the stretching vibration of the C═C group.

Furthermore, at (f) 1566 cm$^{-1}$ the bands corresponding to the bending vibration of N—H and stretching vibration of C—N groups can also be observed. Additionally, it is noted the disappearance of the broad band corresponding to the —OH groups, and the appearance of a sharper band characteristic of the stretching vibration of the —NH group. At (g) 817 cm$^{-1}$ appears the band corresponding to the bending vibration of the double bonds of methacrylate group. The strong band characteristic of isocyanate group (2270 cm$^{-1}$) is not visible.

This indicates that all the isocyanate groups were consumed during the modification.

Figure 2:
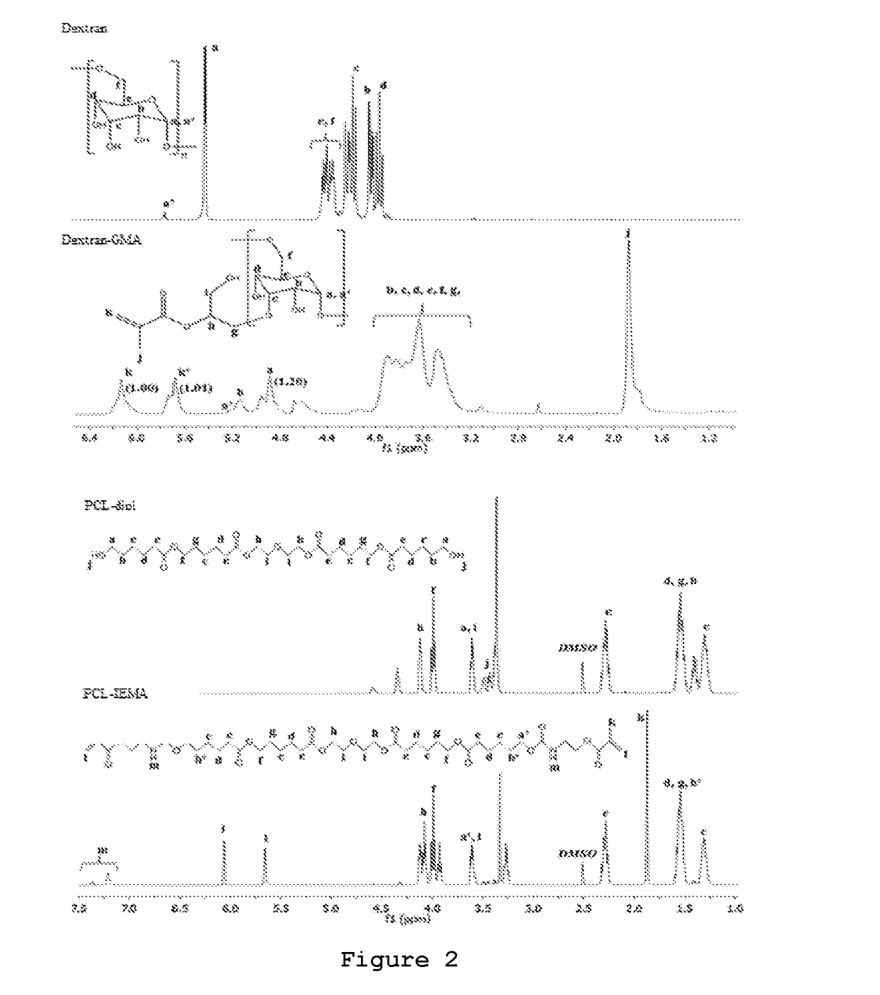
FIG. 2 shows the $^1$H NMR spectra of Dextran, Dextran-GMA, PCL-diol and PCL-IEMA.

$^1$H NMR Spectra of Dextran, Dextran-GMA, PCL-Diol and PCL-IEMA:

In the 1H NMR spectrum of P_LMW in $D_2O$, it can be observed the typical peaks of dextran polymer, which are the multiplet peaks in the range from 4.0 ppm and 3.3 ppm and the anomeric proton peak that is visible at around 5.3 ppm(a').

The spectrum of Dextran-GMA shows additional resonances at ca. 6.1 and 5.7 ppm (k), ascribed to the protons of the double bonds, and at ca. 1.9 ppm (j), corresponding to the protons of the —CH3 group belonging to the methacrylate group. The percentage of modification of dextran was calculated from the relation between the integrals values of the signals corresponding to dextran and to the double bond of GMA.

The $^1$H NMR spectrum of PCL-diol presents the typical resonances of PCL. In the case of PCL-IEMA's 1H NMR spectrum, it is shown clearly the resonance corresponding to the —NH group (m) of the urethane linkage, at 7.2-7.4 ppm. It is also possible to identify the peaks corresponding to the protons of the double bonds (l), at 5.6 and 6.1 ppm, and the peaks of the protons of the —CH3 groups (k), at 1.8 ppm. Moreover, it is possible to see that the resonances corresponding to the protons of the terminal groups in PCL-diol (j) disappeared in the spectrum of PCL-IEMA.

Figure 3:
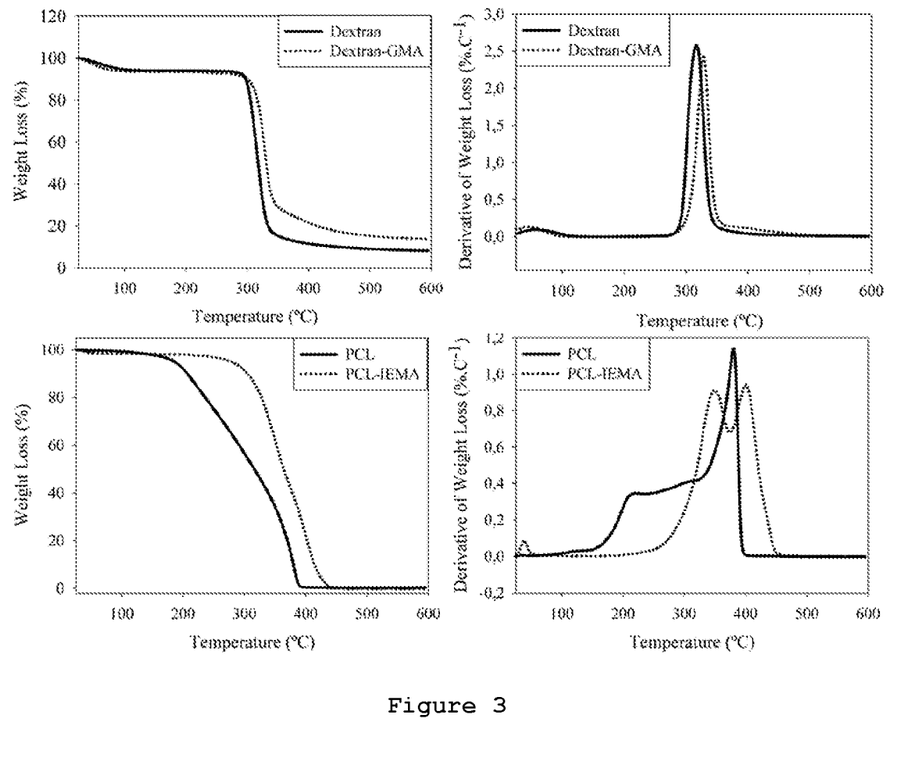
FIG. 3 shows the thermogravimetric curves of Dextran, Dextran-GMA, PCL-diol and PCL-IEMA.

Thermogravimetric Analysis of Dextran-GMA and PCL-IEMA:

The thermoanalytical curve of dextran presents two stages of weight loss. For dextran-GMA GMA, three stages of weight loss can be identified. The first stage of weight loss, between 25 to 150° C., is common to both samples, can be attributed to the loss of residual moisture. The second stage of decomposition, between 270-370° C., refers to the degradation of the polysaccharide dextran chains. This stage of weight loss is also present in both curves. The additional stage of weight loss observed for dextran-GMA can be ascribed to the degradation of the modified part of dextran. These data suggest that the thermal stability of dextran is not affected by the modification with GMA.

The decomposition of PCL-diol occurs in two stages. This can be due to the early degradation of smaller chains present within the PCL-diol matrix. In what concerns PCL_IEMA, it presents also two main stages of weight loss. The first stage (345-350° C.) can be attributed to the decomposition of the urethane bonds, followed by a second stage (378-443° C.) attributed to the degradation of the ester bonds. Also, it can be confirmed, that the sample is free of unreacted IEMA, as there is no peak near its boiling point, 211° C. (Int. J. Pharm 352 (2008) 172-181).

Figure 4:
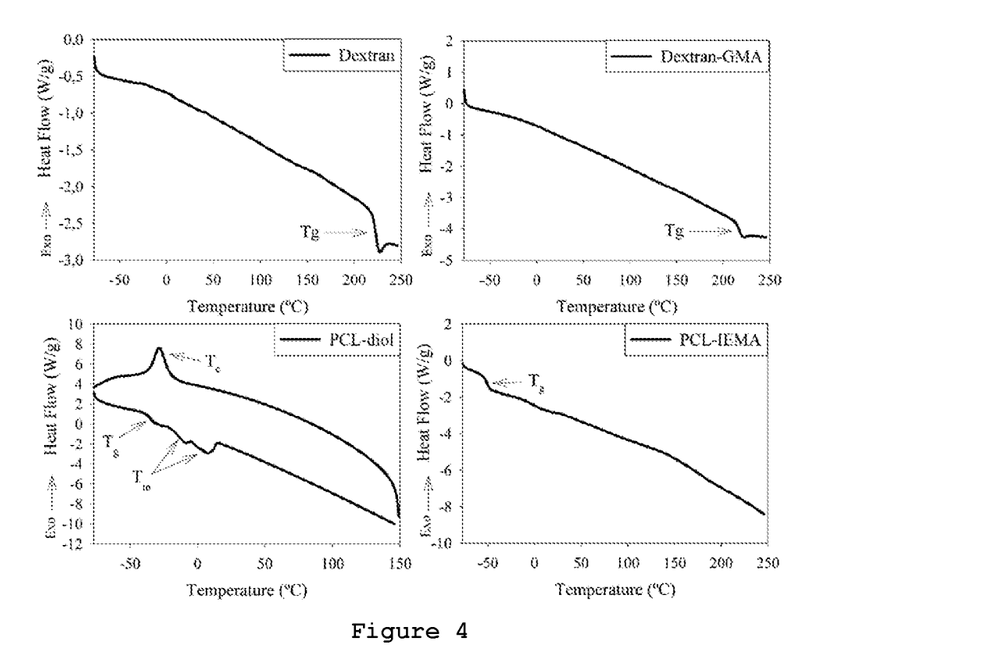
FIG. 4 shows the heat flow curves of Dextran, Dextran-GMA, PCL and PCL-IEMA.

Differential Scanning Calorimetry of Dextran-GMA and PCL-IEMA:

In the heat flow curves of Dextran and Dextran-GMA the only thermal event that can be identified is the Tg, indicating that these materials, as expected, are totally amorphous. On the other hand, the heat flow curves of PCL-diol show one thermal event at −41.0° C., which corresponds to its glass Tg.

Moreover, two other thermal events are present that correspond to the melting (Tm) of the material (−9.0° C. and 7.5° C.) and, in the cooling cycle, to a crystallization (Tc) (−28.6° C.). This fact confirms that PCL-diol is a semi-crystalline polymer. Upon the modification with IEMA, PCL-diol loses its structural order, leading to an amorphous material. In addition, a small decrease in the Tg value is observed (−42.9° C.). The inclusion of IEMA in the PCL-diol structure contributes to an augment in the free volume between the backbone polymeric chains, justifying the observed decrease in the Tg.

Figure 5:
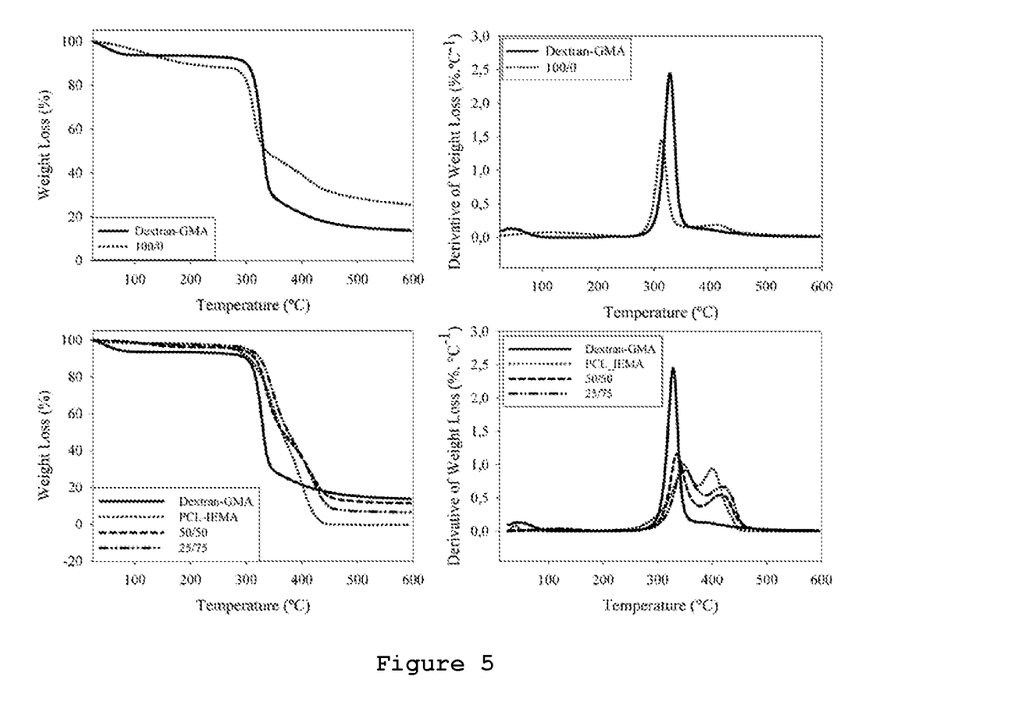
FIG. 5 shows the thermogravimetric curves of copolymers of Dextran-GMA and PCL-IEMA with different co-macromonomer content percentage ratio (using the notation [Dextran-GMA/PCL-IEMA])
  100/0
  50/50
  25/75

Thermogravimetric Analysis of Copolymers:

Copolymers prepared with Dextran-GMA only (100/0) present higher thermal stability in comparison with the corresponding precursor (Dextran-GMA), which is explained by their crosslinked structure (Biomaterials 24 (2003) 759-767). The thermogravimetric curves of copolymers Dextran-GMA and PCL-IEMA with different co-macromonomer content percentage ratio show clearly two stages of weight loss, despite their different compositions. The results show that PCL-IEMA increases the copolymers thermal stability, which that PCL-IEMA has a positive influence on thermal stability of the copolymers. Also, copolymers with higher content of PCL-IEMA (25/75) are consistently more stable compared with the ones with lower content (50/50). This behavior may be ascribed to the increasing crosslinking of the final materials. All membranes were found to be thermally stable until temperatures of ca. 300° C.

Figure 6:
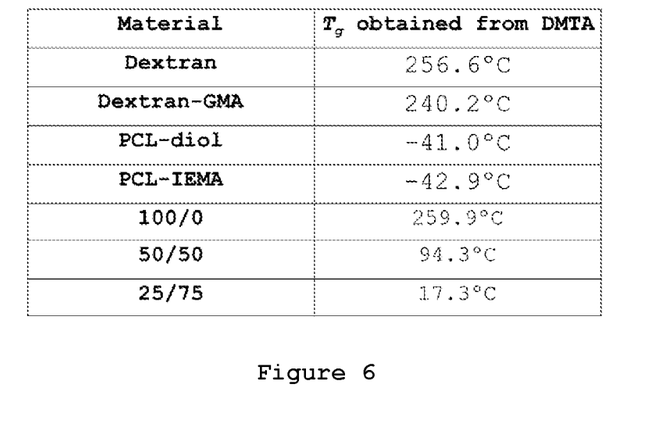
FIG. 6 shows the $T_g$ values of Dextran, Dextran-GMA, PCL-diol, PCL-IEMA and Dextran-GMA:PCL-IEMA copolymers, obtained by dynamic mechanical thermal analysis (DMTA). The DMTA of the samples was conducted in a Tritec2000DMA. The samples were placed in stainless steel material pockets and analyzed in single cantilever mode. The tests were carried out in a temperature range from −150° C. to 300° C., with a heating rate of 10° C.·min−1, in multifrequency mode. The $T_g$ was determined from the peak of tan δ curve, at 1 Hz.

Dynamic Mechanical Thermal Analysis (DMTA):

DMTA analysis show that all materials have a peak corresponding to the Tg. Dextran presents the higher Tg value of all samples. Upon its modification with GMA, the Tg value slightly decreases, as expected. However, between PCL-diol and PCL-IEMA, there is no significant decrease in the Tg value as with inclusion of IEMA contributes to an augment in the free volume between the backbone polymeric chains. Concerning the copolymers Dextran-GMA: PCL-IEMA, the 100/0 formulation (with no PCL-IEMA), has higher Tg than Dextran-GMA, as expected, due to the establishment of a crosslinked network. DMTA analysis of copolymers 50/50 and 25/75 reveal a decrease in their Tg with the increasing content of PCL-IEMA.

Figure 7:
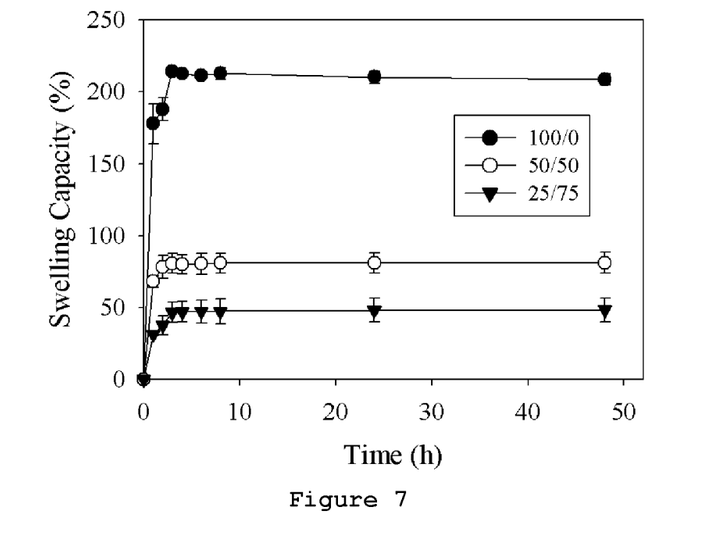
FIG. 7 shows the swelling capacity of copolymers of Dextran-GMA and PCL-IEMA with different co-macromonomer content percentage ratio (using the notation [Dextran-GMA/PCL-IEMA])
  100/0
  50/50
  25/75

Swelling Tests:

With the increase of the content of PCL-IEMA (from 0-75%) in respect to dextran-GMA, the swelling capacity of the final copolymers decreased from 200% to approximately 100%([Dextran-GMA:PCL-IEMA]50:50) and 50%([Dextran-GMA:PCL-IEMA]25:75), as expected due to the hydrophobic character of PCL. Therefore, it is possible to modulate the swelling ability of the materials, which is a very important characteristic for medical applications.

Figure 8:
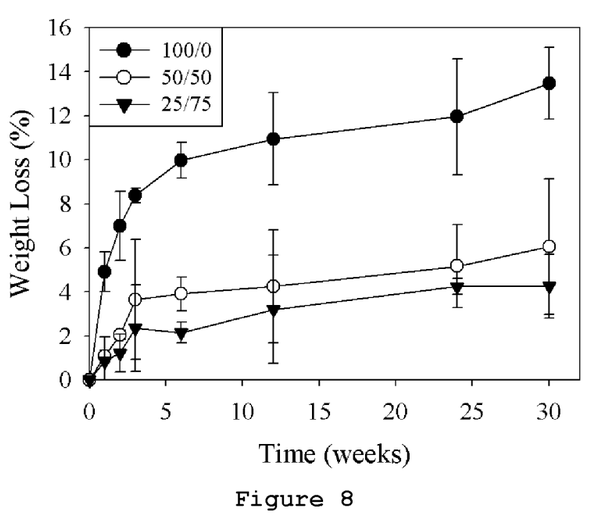

Degradation Tests:

In vitro hydrolytic degradation tests showed that during 30 days, the copolymers lost between 8-12% of their total mass.

In addition, copolymers were able to maintain their structural integrity, showing no signs of cracking or the loss of conformation during this period, and therefore, not compromising its structure and function.

In addition to the promising results obtained from swelling and degradation tests, the copolymers were tested in cellular in vitro tests.

Therefore, it is possible to modulate the degradability by hydrolysis of the materials, which is a very important characteristic for medical applications.

Cell Viability and Cytocompatibility:

The cell viability and cytocompatibility of the copolymers were tested during 7 days. After this time, the viability and proliferation of cells in contact with the materials was analyzed. All materials showed similar cell viability and metabolic rates, in comparison to the control without material which proves the biocompatibility of the prepared materials Therefore, it is possible to modulate the cell viability in contact with the surface of the materials, which is a very important characteristic for in medical applications.

Preliminary In Vivo Tests (Subcutaneous Implants in Rat):

Due to the excellent cell biocompatibility indicators obtained from these copolymers, preliminary in vivo tests were performed.

Samples of the prepared copolymers were subcutaneously implanted in rats and analyzed during 15 days with evaluation of cell count and biological reaction after 3, 7, and 15 days. Upon the end of the test, copolymers constituted only by Dextran-GMA were classified as "slight-irritant" and copolymers with PCL-IEMA in the formulation obtained scores corresponding to the classification of "non-irritant".

In Vivo Tests (Bridging a Nerve Sciatic Gap in Mice)—Tubes Tested as Nerve Tube-Guides:

Concerning the good properties achieved with the copolymers object of this application in relation to swelling capacity, degradation rate, in vitro and in vivo evaluation, the copolymers were shaped into tube forms to be tested as nerve guides.

In what concerns to swelling capacity, both, porous and non-porous tubes, showed values under 60%, being the non-porous tube only 40%, which is an important property in what concerns the behavior on the tube once it is implanted.

Regarding the degradation rates the prepared tubes, the hydrolytic study revealed that after 180 days, they maintained their structural integrity and only lost between 12-16% of their initial weight.

The nerve guide tubes prepared with the copolymers herein described have enough mechanical properties, concerning their resistance to suturing without cracking or breaking, which is an important characteristic for the implantation processes. Additionally, they are able to resist to higher loadings without breaking (2.2-2.4N) than the nerve itself (1-2N).

The performance in vivo of the nerve tube-guides made with these copolymers was evaluated by bridging the sciatic nerve of rats after a neurotmesis injury. For the surgery adult male Sasco Sprague Dawley rats, weighting between 300-350 g, were divided into two groups of six animals each. All animals were housed in a temperature- and humidity-controlled room with 12-12 h light/dark cycles, two animals per cage. Normal cage activities were allowed, under standard laboratory conditions. The animals were fed with standard chow and water ad libitum. Pain and discomfort were minimized by taking the adequate measures taking in consideration human endpoints for animal suffering and distress. Before entering the experience, animals were housed for two weeks.

For surgery, rats were placed prone under sterile conditions. The skin from the clipped lateral right thigh was scrubbed with antiseptic solution, in a routine fashion. Surgeries were conducted under an M-650 operating microscope (Leica Microsystems, Wetzlar, Germany). The anesthesia used was constituted by ketamine 9 mg/100 g; xylazine 1.25 mg/100 g; atropine 0.025 mg/100 body weight, and was applied intramuscularly. Under the effect of anesthesia, a skin incision extending from the greater trochanter to the midhalf distally was made. Then, a muscle-splitting incision was performed to expose the sciatic nerve of the animal. After the immobilization, with the help of straight microsurgical scissors, a transection (neurotmesis) was induced. The nerve was injured immediately above the terminal nerve ramification. In both groups, the proximal and distal stumps were inserted 3 mm into the copolymer D and E nerve guides, and held in place with two epineural sutures using 7/0 monofilament nylon. The nerve gap between the two stumps measured 10 mm. The opposite leg and sciatic nerve were left intact in both groups, and were considered to be the control for normal nerves. A deterrent substance was applied to the right foot of the animals, in order to prevent autotomy. All procedures were conducted with the approval of the Veterinary Authorities of Portugal in accordance with the European Communities Council Directive of November 1986 (86/609/EEC).

The motor performance of the nerve after the neurotmesis injury previous described and repair with nerve tube-guides from this invention was assessed by the conduction of Extensor Postural Thrust (EPT). For the registration of the EPT test results, the body of the rat, with the exception of the hind limbs, is wrapped in a surgical towel. The animal is then supported and lowered by the operator towards the platform of a digital balance. With the approximation to the platform, the animal is allowed to establish visual contact with the platform. Then the animal will anticipate the contact with the platform by extending the hind limb. This contact is made by the distal metatarsus and digits. The weight (force), in grams, applied to the digital platform balance (model TM 560; Gibertini, Milan, Italy) was recorded for both experimental (EEPT) and normal (NEPT) members. Measurements were repeated three times, and the value considered is the mean average between them. The EEPT and NEPT were integrated in the following equation, to obtain the percentage of functional deficit, as reported by Koka et al. (Exp. Neurol 168 (2001) 192-195). After 20 weeks of implantation, an improvement in the percentage of motor recovery over the weeks is observed.

The nociceptive function was assessed by the evaluation of the Withdrawal Reflex Latency (WRL) by the hotplate test modified as described by Masters et al. (Anesthesiology 79 (1993) 340-346). Normal rats withdraw their paws from the hotplate within 4.3s or less. If the withdrawal of the paw did not occur after 12s, the heat stimuli was removed, and the test interrupted to prevent tissue damage. In these cases, the animal was assigned the maximal WRL of 12s. Over time, a tendency in the decrease of WRL is verified.

The static sciatic index (SSI) measurements were taken by the standing of the animals. All footprints were obtained at least during four occasional rest periods. For Measurements were taken from both normal (N) and experimental (E) sides.

Four steps were analyzed per animal and their prints were chosen based on their clarity. The mean distances of the three different measurements taken were used to calculate the following factors: Toe spread factor (TSF), Intermediate toe spread factor (ITSF). The calculation of this parameter was performed using the equation described by Bain (Plast Reconstr Surg 83 (1989) 129-136). The results of these animal tests are summarized in FIGS. 7 to 9.

As evidenced by the results disclosed above, the nerve tube-guides prepared with these copolymers proved to enhance functional recovery of the experimental hind paws as animals were able to produce footprints closer to normal. The materials prepared with copolymers of Dextran-GMA: PCL-IEMA showed excellent biological properties as well as thermomechanical properties (tensile strength, suture strength, glass transition temperature) and swelling properties that can be suitable for the use for medical purposes, particularly, as nerve guides for regenerative medicine.

The copolymer described herein can be processed into films, sheets, tubes, rods, plugs, microspheres or meshes, either solid or porous.

Examples of the other products that can be made from these copolymers are biomedical drains; biomedical tubes for stenting purposes; biomedical sheets for intra-corporeal application such as an anti-adhesive sheet; biomedical sheets for topical use such as temporary wound care coverage or to prevent scarring; wound care foams; protective sheaths for needles and tubes which are introduced into the body; (micro)spheres for drug delivery; (micro)spheres, particles and plugs for embolization purposes; (micro) spheres for cosmetic surgical purposes, such as dermal augmentation, treatment of wrinkles and skin contour deficiencies; vascular prostheses; tissue engineering scaffolds, such as artificial skin or scaffolding plug for meniscus repair.

EXAMPLES

The following notation used is referred to percentage of co-macromonomer in the final composition of copolymers constituted by Dextran-GMA and PCL-IEMA ([Dextran-GMA/PCL-IEMA]).

Example I: Modification of Dextran

Dextran (70.000 g/mol) (Sigma Aldrich, USA) in an amount of 2.5 g (1.54×10−2 mol) was dissolved in 22.5 mL of Dimethyl sulfoxide (DMSO) (Fisher Scientific, EUA) in a round bottom flask. The flask was immersed in a water bath at 30° C. After the complete solubilization of dextran, 0.5 g (4.09×10−3 mol) of 4-Dimethylaminopyridine (DMAP) (TCI Europe, Belgium) was dissolved in the solution and 2.05 mL (1.54×10−2 mol) of Glycidyl methacrylate (GMA) (Acros Organics, Belgium) was added. The reaction proceeded for 8h, under nitrogen atmosphere. After this time, 0.33 mL of hydrochloric acid (HCl) (Fisher Scientific, EUA) 37% (w/w) was added to neutralize the solution. The product of the reaction was then dialyzed against water. The product was freeze dried, leading to a sponge-like product. The notation used to reference of this product was [Dextran-GMA]. The percentage of modification of dextran was obtained by the relation between the integrals values (1H NMR spectrum) of the signals corresponding to dextran and to the double bond of GMA. The obtained values, on average, as sited between 31-34%.

Example II: Modification of Poly (ε-Caprolactone) Diol

In a round bottom flask placed in a water bath at 40° C., 2.2 g (4 mmol) of Poly (ε-caprolactone) diol (PCL-diol)

(Perstorp, UK) was dissolved in 30 mL of Tetrahydrofuran (THF) (VWR, EUA), under nitrogen atmosphere. After PCL-diol solubilization, 1.27 g (8.2 mmol) of 2-Isocyanatoethyl methacrylate (IEMA) (TCI Europe, Belgium) and 150 mg dibutyltin dilaurate (3 drops) (Fluka, USA) were added to the reaction mixture. The reaction was allowed to proceed for 24h. The product was recovered by precipitation in n-hexane (JMGS, Portugal) and dried under vacuum, until constant weight, at room temperature. The notation used for the product that resulted from this procedure was [PCL-IEMA].

In FT-IR spectra of the final product, the strong band characteristic of isocyanate group (2270 cm−1) is not visible. This indicates that all the isocyanate groups were consumed during the modification.

Example III: Copolymer A

Dextran-GMA (0.5 g) was dissolved in 2 mL of DMSO. After dissolution, a biocompatible photoinitiator Irgacure 2959® (Ciba Specialty Chemicals, Switzerland) was added in a concentration of 0.1/w/v (1.11×10−2 mmol). The solution was then placed in a Petri dish and left to photocrosslink in a UV chamber (Model BS-02, from Dr. Grobel, UV-Electronik GmbH), with light with a wavelength of 280 nm, for 2 hours, to yield transparent membranes. The membranes were then washed with distilled water during 7 days. After the washing process, the membranes were cut in circles with a diameter of 1 cm and dried under vacuum, at room temperature, in a desiccator. According to the aforementioned, the notation for this copolymer is 100/0.

Example IV: Copolymer B

Dextran-GMA and PCL-IEMA, in a proportion of 50:50 (w/w), were dissolved in 2 mL of DMSO. After dissolution, photoinitiator Irgacure 2959® (Ciba Specialty Chemicals, Switzerland) was added in a concentration of 0.1/w/v (1.11×10−2 mmol). The solution was then placed in a Petri dish and left to photocrosslink in a UV chamber (Model BS-02, from Dr. Grobel, UV-Electronik GmbH), with light with a wavelength of 280 nm, for 2 hours, to yield transparent membranes. The membranes were then washed with distilled water during 7 days. After the washing process, the membranes were cut in circles with a diameter of 1 cm and dried under vacuum, at room temperature, in a desiccator. According to the aforementioned, the notation for this copolymer is 50/50.

Example V: Copolymer C

Dextran-GMA and PCL-IEMA, in a proportion of 25:75 (w/w), were dissolved in 2 mL of DMSO. After dissolution, photoinitiator Irgacure 2959® (Ciba Specialty Chemicals, Switzerland) was added in a concentration of 0.1/w/v (1.11×10−2 mmol). The solution was then placed in a Petri dish and left to photocrosslink in a UV chamber (Model BS-02, from Dr. Grobel, UV-Electronik GmbH), with light with a wavelength of 280 nm, for 2 hours, to yield transparent membranes. The membranes were then washed with distilled water during 7 days. After the washing process, the membranes were cut in circles with a diameter of 1 cm and dried under vacuum, at room temperature, in a desiccator. According to the aforemention, the notation for this copolymer is 25/75. The composition of copolymers A-C is summarized in Table 1.

TABLE 1

Composition of copolymers A-C

|  | Dextran-GMA (%) | PCL-IEMA (%) |
| --- | --- | --- |
| Copolymer A | 100 | 0 |
| Copolymer B | 50 | 50 |
| Copolymer C | 25 | 75 |

Example VI: Copolymer D

Dextran-GMA and PCL-IEMA, in a proportion of 25:75 (w/w), were dissolved in 2 mL of DMSO. After dissolution, photoinitiator Irgacure 2959® (Ciba Specialty Chemicals, Switzerland) was added in a concentration of 0.1/w/v (1.11×10−2 mmol). The notation for this copolymer is referred to the percentage of co-macromonomers and percentage in weight of D-Mannitol added: [Dextran-GMA/PCL-IEMA (D-Mannitol)](D) 25/75(0).

Example VII: Copolymer E

Dextran-GMA and PCL-IEMA, in a proportion of 25:75 (w/w), were dissolved in 2 mL of DMSO. After dissolution, porogenic agent D-Mannitol (Sigma Aldrich, USA) was added to the mixture (50% w/w). Then, photoinitiator Irgacure 2959® (Ciba Specialty Chemicals, Switzerland) was added in a concentration of 0.1/w/v (1.11×10−2 mmol). The notation for this copolymer is referred to the percentage of co-macromonomers and percentage in weight of D-Mannitol added: [Dextran-GMA/PCL-IEMA(D-Mannitol)](E) 25/75(50)

Example VII: Preparation of Nerve Guide Conduits

Nerve guide conduits were prepared from copolymers D and E. The copolymers were placed into a mold composed of a quartz tube with a stainless steel rod inside to achieve the hollow tube shape. The mold with the copolymers were left to photocrosslink in a UV chamber (Model BS-02, from Dr. Grobel, UV-Electronik GmbH, with a wavelength of 280 nm), for 20 minutes. After that time, the nerve guides were demolded and left in absorbent paper for 2 days to eliminate the excess DMSO. Then, nerve guides were washed with Milli-Q water. In the case of copolymer E, to remove D-mannitol, after the polymerization, the resulting materials were immersed in distilled water and left in an oven at 37° C. for 3 days. Then, copolymer E was washed with Milli-Q water for 7 days.

The nerve guides were dried under vacuum, at 40° C. After the drying process, segments of tubes with 1 cm were cut for characterization.

FIG. 1 shows the swelling capacity of copolymers A-C. The three copolymers stabilized their swelling capacity after approximately 2-3 hours.

Dextran is well known for its high affinity with water, which explains the higher swelling capacity presented by copolymer A (100/0). In turn, it was verified that with the increase of the hydrophobic PCL-IEMA content in the formulation of the copolymers B and C, the swelling capacity decreases (from ca. 200% to 100-50% approximately).

FIG. 2 presents the in vitro hydrolytic degradation of copolymers A-C under simulated physiological conditions (PBS, pH=7.4, 37° C.).

Copolymer A presents higher degradation rate compared with copolymers B and C. As aforementioned, dextran has high affinity with water, leading to high swelling capacity values, which favors the degradation ratio. Upon the incorporation of PCL-IEMA, a decrease in the weight loss is observed. The hydrophobic nature of PCL-IEMA does not allow the degradation medium to easily penetrate in the crosslinked network, leading to a decrease in the weight loss values.

FIG. 3 plots the absorbance assessed by Presto Blue® viability assay of human dental pulp stem cells (hDPSCs) seeded in copolymers A-C. The results show that the fixation agent used to fix the membranes to the cell culture plate does not significantly affect cell adhesion and cell metabolism as compared to the control at any time point. This can be observed by the similarity of absorbance values obtained for the control (Ct) with the values obtained for the control with the fixation agent (Ct SG).

It is noteworthy the fact that cell adhesion to the membranes upon seeding is significantly inferior to the control and to the fixation agent control.

At later incubation time (at 5 and 7 days) copolymer C shows improved cell viability and metabolic activity as compared to the control.

At 5 days incubation, it was reached the maximum absorbance and cell metabolic activity measure. This is due to the fact that cells reached their confluence between 5 and 7 days period leading to an arrest on cell metabolic activity due to the lack of available surface space.

FIG. 4 shows the histologic scores of copolymers A-C, obtained following ISO 10993-6:2016 Part 6: Tests for local effects after implantation).

Upon euthanasia, exposed subcutaneous tissue presented smooth, with no visible signs of hemorrhage or inflammation. In all groups, copolymers were involved by a thin, transparent capsule of subcutaneous tissue.

Microscopically, at 3 days after implantation, a mixed cellular infiltrate was observed in all groups. However, at this time point, a predominance of mononuclear inflammatory cells, such as macrophages and lymphocytes, was present in both sham and copolymers. Minimal necrosis events were observable in all groups (sham: 0.139; copolymer A: 0.563; copolymer B: 0.389, and copolymer C: 0.045; mean score out of a maximum 4 score). Regarding fibrosis, all groups, including Sham, scored under 1.4 out of 4 mean scores.

At 7 days implantation, an acute inflammatory response is still detectable with continuing dominance of mononuclear cells. Necrosis findings decrease significantly in almost all samples and sham, except for copolymer C, in which values reach 0.450, out of 4 mean scores. Regarding fibrosis, all samples and sham maintain the scores of the 3 days group analysis.

After 15 days implantation, an expected decrease in polymorphonuclear leukocytes was observed in almost all groups except copolymer A. In addition, a moderate chronic response mainly constituted by lymphocytic aggregates is still detectable in all groups tested. At this time, no necrosis is observed in copolymer A and copolymer C samples (0.00 mean scores), although copolymer B reveal residual necrosis score values (0.059), lower than the observed in sham (0.091).

Fibrosis remained under 1.9 with in all groups. A slight increase in vascularization was observed in copolymer C, and a slight decrease was recorded for copolymer A.

According to the standard guidelines, at 3 and 15 days copolymer A scored as "slight irritant", and at 7 days, both copolymer A and copolymer C scored as "slight irritant". All other samples scored as "non-irritant". The calculated scores show that copolymers B and C are considered to be "non-irritant". From this figure it is inferred that the copolymers herein described showed very low immune response with improved properties with respect to body rejection.

FIG. 5 plots the swelling capacity of copolymers D and E, evaluated in PBS (pH=7.4), at 37° C. The results show that the swelling capacity of the nerve guides stabilize approximately after 4-5 hours of immersion. Copolymer D presents a swelling capacity around 40%, while the value obtained for copolymer E is ca. 60%. In the dark light images, (a) presents the nerve guide in the dry state, and (b) in the wet state. Is clear that the dimension of the inner diameter of tube is not compromised after swelling (b) equilibrium is achieved. Likewise, the inner diameter increases, which will be useful for implantation purposes.

FIG. 6 presents the in vitro hydrolytic degradation of the nerve guides prepared with copolymer D and E, under simulated physiological conditions (PBS, pH=7.4, 37° C.).

After 180 days, it is possible to see that copolymer D lost around 16% of its mass, and copolymer E lost around 13%. Both profiles indicate that both nerve guides can degrade consecutively with no significant alterations on the degradation rates until 100 days. From this figure, it follows that the nerve guides prepared with the copolymers of this invention showed a pattern of degradation compatible with the ones observed for the materials and with good values for the process of implantation.

FIG. 7 plots the percentage of motor deficit, which results from the EPT measurements. Despite the oscillating values resulting from the difficulty in ensuring equal movements of the animals during limb extension, linear regression traces show a general tendency for a decrease in the percentage of motor deficit value in both groups. Thus, an improvement in the percentage of motor recovery over the weeks is observed. From this figure it follows that the nerve guides prepared with the copolymers of this invention contributes to a significantly enhancement of the T, the recovery of motor function.

FIG. 8 shows the WRL values obtained by the use of a painful stimuli. The linear regression lines demonstrate a tendency of decrease of WRL over time. This means that an improvement in the sensorial function was observed. Despite the oscillating values, at week-20 all animals took less time to respond to the stimuli, in comparison with the first time point. From this figure it follows that the nerve guides prepared with the copolymers of this invention when implanted in rats contributes to recover the sensitive function expressed in the WRL values to a level close to the healthy ones.

Figure 9:
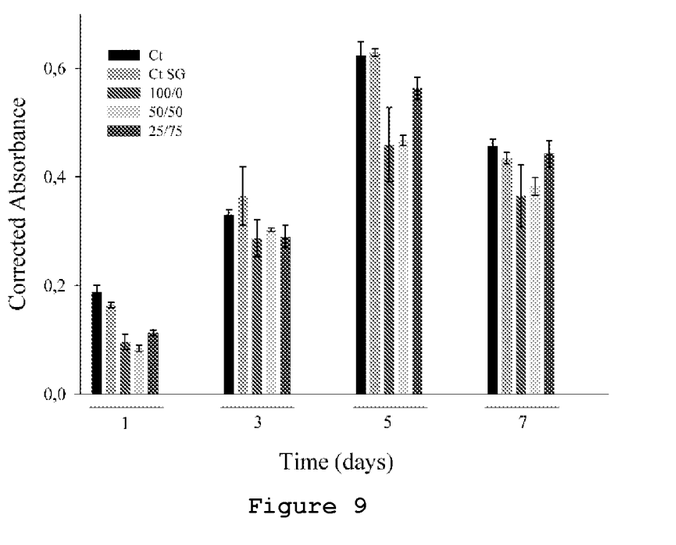
FIG. 9 shows the absorbance assessed by Presto Blue® viability assay of human dental pulp stem cells (hDPSCs) seeded in copolymers. The notation used refers to the percentage of co-macromonomer in the final composition of the material ([Dextran-GMA/PCL-IEMA]).
Figure 10:
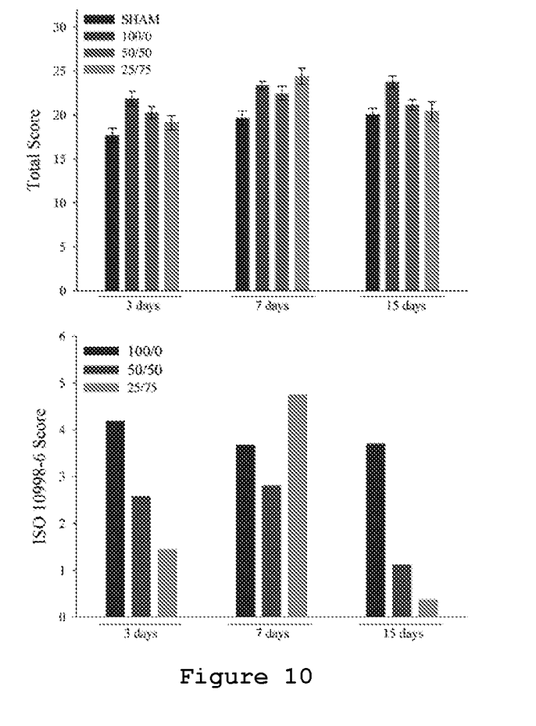
FIG. 10 shows the histological scores obtained from subcutaneous implantation of Dextran-GMA and PCL-IEMA copolymers. The notation used is referred to the co-macromonomer ratio in the final composition of the material. The scores were obtained following ISO 10998-6 score system. "SHAM" refers to the control—incision without implant.
Figure 11:
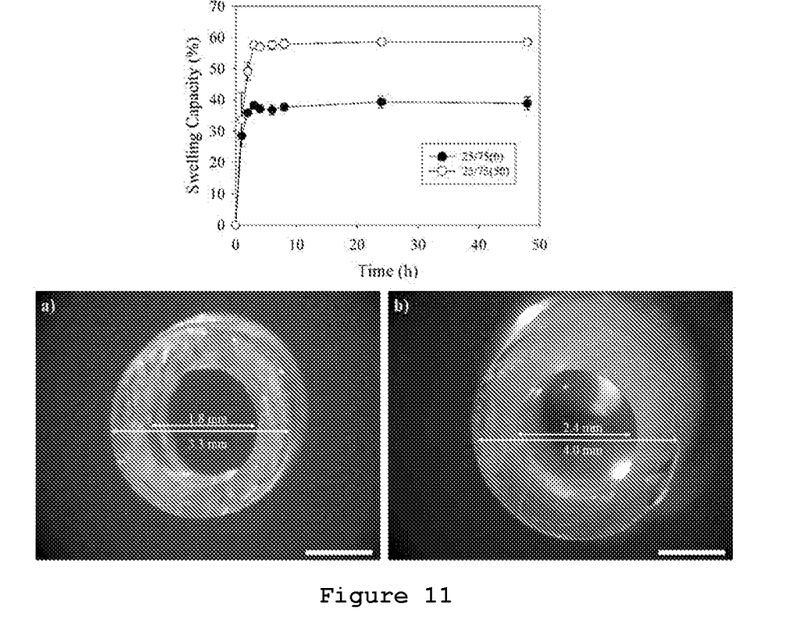
FIG. 11 presents the percentage of swelling capacity of nerve guide conduits prepared using the Dextran-GMA/PCL-IEMA copolymer (25/75) with porogenic agent D-Mannitol. The notation used is referred to the percentage content of Dextran-GMA:PCL-IEMA and the and content of D-Mannitol added (in percentage): ([Dextran-GMA/PCL-IEMA](D-Mannitol)
  25/75(0)
  25/75(50)
Figure 12:
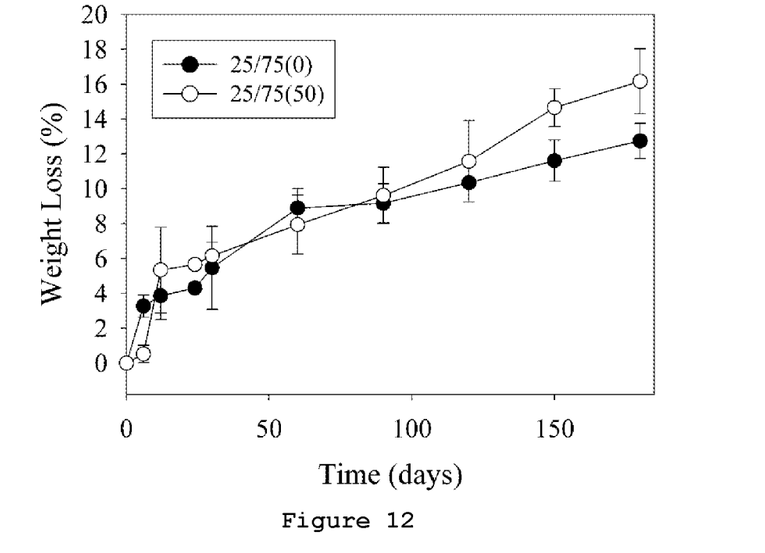
FIG. 12 shows the in vitro hydrolytic degradation of copolymers of Dextran-GMA and PCL-IEMA with tube shape conformation. The following notation is used to indicate the co-macromonomer content percentage ratio in the final composition of the copolymers, and content of D-Mannitol: [Dextran-GMA/PCL-IEMA](D-Mannitol).
Figure 13:
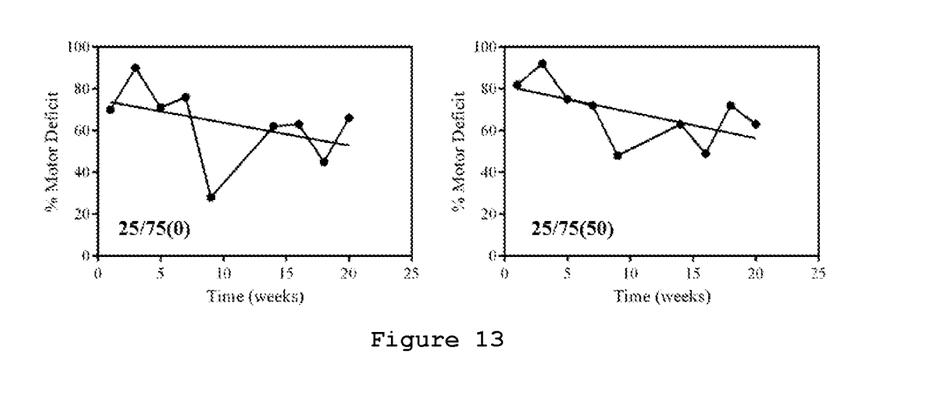
FIG. 13 shows the percentage of motor deficit after during the period the rat sciatic nerve was bridged by copolymers nerve guides. The following notation is used to indicate the co-macromonomer content percentage ratio in the final composition of the copolymers, and content of D-Mannitol: [Dextran-GMA/PCL-IEMA](D-Mannitol).
Figure 14:
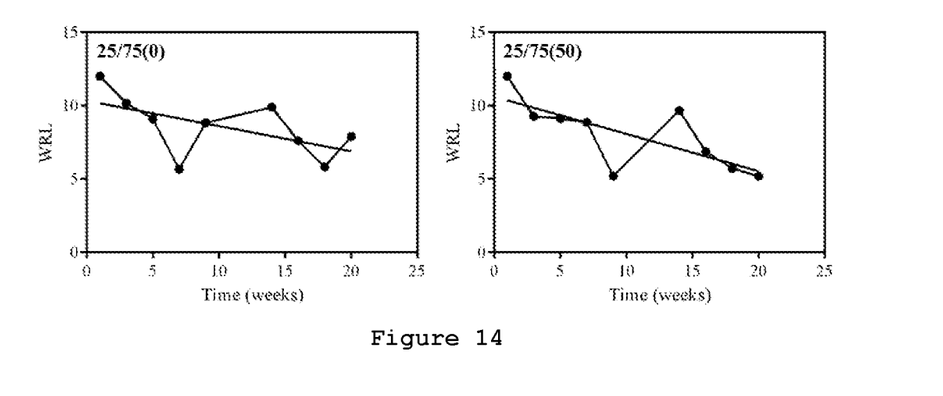
Figure 15:
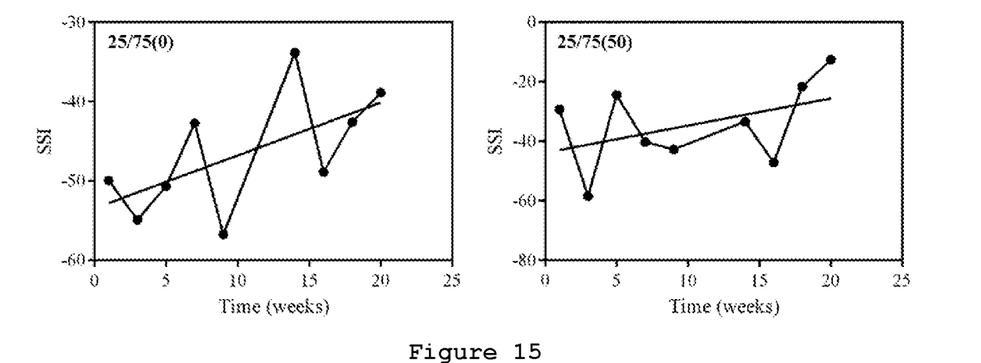
FIG. 15 shows the static functional index given by the footprints of the rats during the period the rat sciatic nerve was bridged by copolymers nerve guides. The following notation is used to indicate the co-macromonomer content percentage ratio in the final composition of the copolymers, and content of D-Mannitol: [Dextran-GMA/PCL-IEMA](D-Mannitol).

FIG. 9 presents the SSI values obtained by the analysis of the footprints of standing rats. Linear regression traces show that for both copolymers there are a tendency for the mean values of SSI to increase over time. This means that functional recovery was consistently achieved. Also, animals that received both nerve guides show superior SSI at the end of the experiment comparing with the first week after surgery. From this figure it follows that the nerve guides prepared with the copolymers of this invention when implanted in rats contributes to recover the sensitive function expressed in their experimental footprints became more similar to normal footprints.

Although the preferred embodiments of the present application have been disclosed for illustrative purposes, those skilled in the art will appreciate that various modifications, additions and substitutions are possible, without departing from the scope of the invention. Therefore, the present invention is not limited to the above-described embodi-

The invention claimed is:

1. A photopolymerized biodegradable copolymer formulations comprising dextran modified with glycidylmethacrylate and poly e-caprolactone modified with 2-isocyanatoethyl methacrylate.

2. The copolymer formulations according to claim 1, wherein the percentage of the modified dextran ranges between 25% and 50% (w/w).

3. The copolymer formulations according to claim 1, wherein the percentage of the modified poly e-caprolactone ranges between 50% and 75% (w/w).

4. The copolymer formulations according to claim 1, wherein the formulations further comprise water soluble sugar-type or salt-type known porogenic agents.

5. The copolymer formulations according to claim 4, wherein the porogenic agent is selected from the group consisting of sucrose, sodium chloride and sodium carbonate.

6. The copolymer formulations according to claim 4, wherein the porogenic agent is D-mannitol.

7. The copolymer formulations according to claim 6, wherein the content of D-mannitol ranges between 20 and 80% (w/w) of the copolymer formulation.

8. The copolymer formulations according to claim 1, wherein the copolymer is shaped into films, sheets, tubes, rods, plugs, microspheres, 3-D scaffolds, or meshes.

9. The copolymer formulations according to claim 1, wherein the copolymer formulations are solid.

10. A method of photopolymerization to prepare solid materials from copolymer formulations according to claim 1, comprising the following steps:
dissolving dextran modified with glycidyl methacrylate in DMSO at room temperature to obtain a solution;
adding poly e-caprolactone modified with 2-isocyanatoethyl methacrylate to the solution obtained from the previous step thereby obtaining co-macromonomers;
carrying out a complete dissolution of the co-macromonomers obtained from the previous step and adding a photoinitiator thereby obtaining a formulation;
leaving the formulation to photocrosslink under UV light with a wavelength of 280 nm to obtain a copolymer; and
washing the copolymer with water for a period up to 7 days and then drying under vacuum.

11. The method according to claim 10, wherein dextran in a range up to 200000 g/mol is used.

12. The method according to claim 10, wherein dextran 70000 g/mol is used.

13. The method according to claim 10, wherein poly e-caprolactone in a range up to 600 g/mol is used.

14. The method according to claim 10, wherein the final copolymer formulations are dried at 40° C.

15. The method according to claim 10, wherein the photoinitiator is used in a concentration between 0.02 and 2% (w/v).

16. The method according to claim 10, wherein after complete dissolution of the co-macromonomers, a water soluble sugar-type or salt-type known porogenic agent is added to the solution and left to solubilize.

17. The method according to claim 16, wherein the copolymer comprising the porogenic agent are immersed in distilled water and left in an oven at 37° C. for 3 days, before washing the final copolymer with water and drying under vacuum.

18. A method for use as biomedical drains, for biomedical tubes for stenting purposes, biomedical sheets for intracorporeal application such as an anti adhesive sheet, for biomedical sheets for topical use such as temporary wound care coverage or to prevent scarring, for wound care foams, for protective sheaths for needles and tubes which are introduced into the body, for (micro) spheres for drug delivery, (micro) spheres, particles and plugs for embolization purposes, (micro) spheres for cosmetic surgical purposes, such as dermal augmentation, for treatment of wrinkles and skin contour deficiencies, for vascular prostheses, tissue engineering scaffolds, artificial skin or scaffolding plug for meniscus repair comprising applying the photopolymerized biodegradable copolymer formulation according to claim 1.

* * * * *